(12) United States Patent
Kocher (10) Patent No.: US 12,422,420 B2
(45) Date of Patent: *Sep. 23, 2025

(54) PROGRAMMABLE LOGIC CONTROLLER-BASED SYSTEM AND USER INTERFACE FOR AIR SAMPLING IN CONTROLLED ENVIRONMENTS

(71) Applicant: Veltek Associates, Inc., Malvern, PA (US)

(72) Inventor: Nathan G. Kocher, West Chester, PA (US)

(73) Assignee: Veltek Associates, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/635,145

(22) Filed: Apr. 15, 2024

(65) Prior Publication Data
US 2024/0272131 A1 Aug. 15, 2024

Related U.S. Application Data

(63) Continuation of application No. 17/070,506, filed on Oct. 14, 2020, now Pat. No. 11,971,396, which is a
(Continued)

(51) Int. Cl.
*G01N 33/00* (2006.01)
*F24F 3/167* (2021.01)
(Continued)

(52) U.S. Cl.
CPC .......... *G01N 33/0011* (2013.01); *F24F 3/167* (2021.01); *F24F 11/50* (2018.01);
(Continued)

(58) Field of Classification Search
CPC .. G01N 33/0011; G01N 33/0073; G01N 1/22; G01N 1/24; G01N 1/26;
(Continued)

(56) References Cited

U.S. PATENT DOCUMENTS

| | | |
|---|---|---|
| 3,693,706 A | 9/1972 | Nisley |
| 3,719,321 A | 3/1973 | McNabney |

(Continued)

FOREIGN PATENT DOCUMENTS

| | | |
|---|---|---|
| CN | 2074015 U | 3/1991 |
| CN | 1146001 | 3/1997 |

(Continued)

OTHER PUBLICATIONS

Bernoulli's equation. (2008). In D. Nelson (Ed.), The Penguin dictionary of mathematics (4th ed.). 1 page. Penguin. Credo Reference: https://search_credoreference.com/content/entry/penguinmath/bernoulli_s_equation/0?instituionId=743.
(Continued)

*Primary Examiner* — M. N. Von Buhr
(74) *Attorney, Agent, or Firm* — Blank Rome LLP (57) ABSTRACT

A system and method for sampling air at multiple locations in a controlled environment. The system and method includes automatic adjustment of mass flow rates and duration of vacuum connections (either via time elapsed or indirectly by volume) based on rates set by an operator. Additionally, the system and method enables users to monitor and control aspects of the system via network-connected devices. Additionally, the system enable a vacuum pump to be disconnected from power in response to a physical emergency button, a software-based emergency stop button available on network connected devices, and an automatic power disconnection in response to an abnormal mass flow reading that could potentially impact the vacuum pump.

20 Claims, 6 Drawing Sheets

Related U.S. Application Data continuation of application No. 15/946,461, filed on Apr. 5, 2018, now abandoned, which is a continuation of application No. 14/471,848, filed on Aug. 28, 2014, now Pat. No. 9,939,416.

(51) Int. Cl.
| | | |
|---|---|---|
| *F24F 11/00* | (2018.01) | |
| *F24F 11/50* | (2018.01) | |
| *F24F 11/74* | (2018.01) | |
| *G01N 1/22* | (2006.01) | |
| *G01N 1/24* | (2006.01) | |
| *G01N 1/26* | (2006.01) | |
| *G05D 7/06* | (2006.01) | |

(52) U.S. Cl.
CPC .......... *F24F 11/74* (2018.01); *G01N 1/2273* (2013.01); *G01N 1/24* (2013.01); *G01N 1/26* (2013.01); *G01N 33/0073* (2013.01); *G05D 7/0623* (2013.01); *F24F 2011/0005* (2013.01)

(58) Field of Classification Search
CPC ........ G01N 1/2273; F24F 3/161; F24F 3/167; F24F 11/50; F24F 11/74; F24F 2011/0005; G05D 7/0623; Y10S 2/901; Y02B 30/70
See application file for complete search history.

(56) References Cited

U.S. PATENT DOCUMENTS

| | | | |
|---|---|---|---|
| 3,748,906 A | 7/1973 | Manka | |
| 3,950,946 A | 4/1976 | Sakai | |
| 3,950,948 A | 4/1976 | Luke | |
| 4,091,674 A | 5/1978 | Amey | |
| 4,246,788 A | 1/1981 | Olin | |
| 4,604,111 A | 8/1986 | Natale | |
| 4,663,293 A | 5/1987 | Hempel | |
| 4,747,315 A | 5/1988 | Padden | |
| 4,804,391 A | 2/1989 | Griffis | |
| 4,813,984 A | 3/1989 | Griffis | |
| 5,076,761 A | 12/1991 | Krohn | |
| 5,183,983 A | 2/1993 | Knop | |
| 5,195,922 A | 3/1993 | Genco | |
| 5,230,080 A | 7/1993 | Fabre | |
| 5,246,668 A | 9/1993 | MacCallum | |
| 5,421,214 A | 6/1995 | Burgdorfer | |
| 5,502,998 A | 4/1996 | Miller | |
| 5,553,496 A | 9/1996 | Nishiyama | |
| 5,576,946 A | 11/1996 | Bender | |
| 5,591,974 A | 1/1997 | Troyer | |
| 5,635,403 A | 6/1997 | Bailey | |
| 5,645,480 A | 7/1997 | Spengler | |
| 5,831,182 A | 11/1998 | Swenson | |
| 5,838,008 A | 11/1998 | Esler | |
| 5,845,480 A | 12/1998 | DeFreitas | |
| 5,931,227 A | 8/1999 | Graves | |
| 6,059,536 A | 5/2000 | Stingl | |
| 6,125,710 A | 10/2000 | Sharp | |
| 6,167,107 A | 12/2000 | Bates | |
| 6,167,766 B1 | 1/2001 | Dunn | |
| 6,187,107 B1 | 2/2001 | Duchi | |
| 6,192,922 B1 | 2/2001 | MacGibbon | |
| 6,216,548 B1 | 4/2001 | Park | |
| 6,230,080 B1 | 5/2001 | Lee | |
| 6,245,297 B1 | 6/2001 | Kowallis | |
| 6,264,111 B1 | 7/2001 | Nicolson | |
| 6,295,864 B1 | 10/2001 | You | |
| 6,295,884 B1 | 10/2001 | Miyake | |
| 6,425,297 B1 | 7/2002 | Sharp | |
| 6,425,298 B1 | 7/2002 | Jackson | |
| 6,514,721 B2 | 2/2003 | Spurrell | |
| 6,532,835 B1 | 3/2003 | Saaski | |
| 6,692,953 B1 | 2/2004 | Sugita | |
| 6,867,682 B2 | 3/2005 | Reinhardt | |
| 6,997,053 B2 | 2/2006 | Forshey | |
| 7,113,895 B2 | 9/2006 | Tariq | |
| 7,127,847 B2 | 10/2006 | Fitzgibbon | |
| 7,340,311 B2 | 3/2008 | Landis | |
| 7,393,390 B2 | 7/2008 | Matsunaga | |
| 7,667,839 B2 | 2/2010 | Bates | |
| 7,813,822 B1* | 10/2010 | Hoffberg | H04N 7/163 381/73.1 |
| 7,867,839 B2 | 1/2011 | Chen | |
| 7,940,188 B2 | 5/2011 | Calio | |
| 7,973,668 B2 | 7/2011 | Calio | |
| 8,006,542 B2 | 8/2011 | Jones, Jr. | |
| 8,169,330 B2 | 5/2012 | Calio | |
| 8,188,874 B2 | 5/2012 | Calio | |
| 8,199,003 B2 | 6/2012 | Aaron | |
| 8,356,623 B2 | 1/2013 | Isobe | |
| 8,701,980 B2 | 4/2014 | Calio | |
| 8,904,849 B2 | 12/2014 | Norman | |
| 9,043,161 B2 | 5/2015 | Jeffers | |
| 9,063,040 B2 | 6/2015 | Calio | |
| 9,109,981 B2 | 8/2015 | Sharp | |
| 9,223,318 B2 | 12/2015 | Takeuchi | |
| 9,285,792 B2* | 3/2016 | Churchvara | G08B 21/12 |
| 9,371,828 B2 | 6/2016 | Tsai | |
| 9,651,038 B2 | 5/2017 | Szpak | |
| 9,939,416 B2 | 4/2018 | Kocher | |
| 10,139,318 B2 | 11/2018 | Calio | |
| 10,677,691 B2* | 6/2020 | Calio | G01N 1/24 |
| 10,732,081 B2* | 8/2020 | Kocher | G01N 1/2273 |
| 11,454,573 B2* | 9/2022 | Calio | G01N 1/24 |
| 11,808,674 B2* | 11/2023 | Calio | G08B 21/182 |
| 11,971,396 B2* | 4/2024 | Kocher | G01N 1/24 |
| 2001/0004842 A1 | 6/2001 | Krajewski | |
| 2001/0013245 A1 | 8/2001 | Hanashiro | |
| 2001/0030642 A1 | 10/2001 | Sullivan | |
| 2002/0070862 A1 | 6/2002 | Francis | |
| 2002/0178789 A1 | 12/2002 | Sunshine | |
| 2002/0184957 A1 | 12/2002 | Kuhn | |
| 2003/0010918 A1 | 1/2003 | Komiyama | |
| 2003/0054561 A1 | 3/2003 | Gelernt | |
| 2004/0051739 A1 | 3/2004 | Schmickley | |
| 2004/0182096 A1 | 9/2004 | Alles | |
| 2005/0024216 A1 | 2/2005 | Crooks | |
| 2005/0136146 A1* | 6/2005 | Pham | D06Q 1/00 425/127 |
| 2005/0156730 A1 | 7/2005 | Chapman, Jr. | |
| 2006/0000296 A1 | 1/2006 | Salter | |
| 2006/0060005 A1 | 3/2006 | Desrochers | |
| 2006/0097860 A1 | 5/2006 | Halfmann | |
| 2006/0173579 A1 | 8/2006 | Desrochers | |
| 2006/0234621 A1 | 10/2006 | Desrochers | |
| 2007/0021050 A1 | 1/2007 | Kennedy | |
| 2007/0107450 A1 | 5/2007 | Sasao | |
| 2007/0113686 A1 | 5/2007 | Desrochers | |
| 2007/0131887 A1 | 6/2007 | Huang | |
| 2008/0054082 A1 | 3/2008 | Evans | |
| 2008/0084895 A1 | 4/2008 | Lee | |
| 2008/0148816 A1 | 6/2008 | Groves | |
| 2008/0180243 A1 | 7/2008 | Aaron | |
| 2008/0229805 A1 | 9/2008 | Barket | |
| 2008/0281528 A1 | 11/2008 | Relle, Jr. | |
| 2008/0314461 A1 | 12/2008 | Moretto | |
| 2009/0032126 A1 | 2/2009 | Kissel, Jr. | |
| 2009/0261174 A1 | 10/2009 | Butler | |
| 2009/0302249 A1 | 12/2009 | Fincher | |
| 2010/0022965 A1 | 1/2010 | Salzman | |
| 2010/0078493 A1 | 4/2010 | Alles | |
| 2010/0094565 A1 | 4/2010 | Prince | |
| 2010/0171625 A1 | 7/2010 | Calio | |
| 2010/0212436 A1* | 8/2010 | Swenson | G01N 1/2208 73/863.22 |
| 2010/0229965 A1 | 9/2010 | Kashima | |
| 2010/0256821 A1 | 10/2010 | Jeung | |
| 2010/0289653 A1 | 11/2010 | Calio | |
| 2011/0088490 A1 | 4/2011 | Ludwick | |
| 2011/0184564 A1 | 7/2011 | Amundson | |
| 2011/0192213 A1 | 8/2011 | Zimmerman | |
| 2011/0223581 A1 | 9/2011 | Stobbe | |

(56) References Cited

U.S. PATENT DOCUMENTS

| | | |
|---|---|---|
| 2011/0252897 A1 | 10/2011 | Swenson |
| 2011/0300790 A1 | 12/2011 | Bauer |
| 2012/0152040 A1 | 6/2012 | Calio |
| 2012/0212342 A1 | 8/2012 | Aaron |
| 2012/0218023 A1 | 8/2012 | Trock |
| 2012/0218102 A1 | 8/2012 | Bivens |
| 2012/0289139 A1 | 11/2012 | Fujimura |
| 2013/0046485 A1 | 2/2013 | Norman |
| 2013/0093381 A1 | 4/2013 | Mcginley |
| 2013/0161403 A1 | 6/2013 | Douglas |
| 2013/0205822 A1 | 8/2013 | Heiland |
| 2014/0132415 A1 | 5/2014 | Churchvara |
| 2015/0185194 A1 | 7/2015 | Prince |
| 2015/0315803 A1 | 11/2015 | Hamza |
| 2015/0355000 A1 | 12/2015 | Bates |
| 2016/0151741 A1 | 6/2016 | Zhu |
| 2016/0153948 A1 | 6/2016 | Churchvara |
| 2018/0120278 A1 | 5/2018 | Hoorfar |
| 2018/0224413 A1 | 8/2018 | Kocher |
| 2022/0113225 A1 | 4/2022 | Calio |
| 2023/0258541 A1* | 8/2023 | Kocher ............... G01N 1/2273 73/31.02 |
| 2024/0068916 A1* | 2/2024 | Calio ................... G01N 1/24 |

FOREIGN PATENT DOCUMENTS

| | | |
|---|---|---|
| CN | 1260041 | 7/2000 |
| CN | 1598591 A | 3/2005 |
| CN | 1714917 A | 1/2006 |
| CN | 101315315 A | 12/2008 |
| CN | 201377875 Y | 1/2010 |
| CN | 102066897 A | 5/2011 |
| CN | 201983961 U | 9/2011 |
| CN | 202066897 A | 12/2011 |
| CN | 102859562 A | 1/2013 |
| CN | 103876744 A | 6/2014 |
| EP | 2343528 A2 | 7/2011 |
| JP | S5420789 | 2/1979 |
| JP | H01261832 A | 10/1989 |
| JP | H07209146 A | 8/1995 |
| JP | H0886877 A | 4/1996 |
| JP | 2002174570 | 6/2002 |
| JP | 2003065577 A | 3/2003 |
| JP | 2003215001 A | 7/2003 |
| JP | 2009011265 A | 1/2009 |
| JP | 2012237527 A | 12/2012 |
| WO | 2009100184 A1 | 8/2009 |
| WO | 2010105161 A1 | 9/2010 |
| WO | 2011010314 | 1/2011 |
| WO | 2011059308 A2 | 5/2011 |
| WO | 2011103145 A1 | 8/2011 |
| WO | 2014003628 A1 | 1/2014 |
| WO | 2014074718 A2 | 5/2014 |
| WO | 2016032903 A1 | 3/2016 |

OTHER PUBLICATIONS

Copley Scientific, Quality Solutions for Air Sampling & Particle Analysis, 2006 Edition, Copley Scientific AG, www.copleyscientific.com, pp. 1-27.
Decision of Dismissal for JP 2017-511659, dated Mar. 29, 2021, 8 pgs.
Environmental Control Monitoring Division, Veltek Associates, Inc, http://web.archive.Org/web/20081010142807/http://www.sterile.com/pages/products/products-environmental-control-monitoring.htm, 2 pages, Oct. 10, 2008.
EP Communication for EP Application No. 10751476.2, dated Nov. 26, 2020, 10 pgs.
European Search Report for Application No. EP19183804.4, dated Jul. 10, 2019, 8 pgs.
European Search Report for EP Application No. 21158019.6, dated Jun. 18, 2021. 6 pages.
Examination Report No. 1 for AU Application No. 2020202115, dated Mar. 23, 2021, 4 pages.
Examiner's Report for CA 2,957,083, dated Aug. 20, 2021, 3 pgs.
Extended European Search Report for EP Application No. 09708428.9, dated Jul. 3, 2017; 9 pages.
Extended European Search Report for EP Application No. 10751476.2, dated Oct. 3, 2017, 10 pages.
Extended European Search Report for EP Application No. 11745152.6, dated Oct. 26, 2017, 8 pages.
Final Office Action for JP Application No. 2017-511659, dated Aug. 17, 2020, 8 pages.
Final Office Action received in U.S. Appl. No. 15/946,461, dated Oct. 5, 2021. 14 pages.
International Appl. No. PCT/US2015/046365, International Search Report and Written Opinion, dated Nov. 27, 2015, 12 pages.
International Preliminary Report on Patentability received in PCT Application No. PCT/US2015/046365, dated Feb. 28, 2017. 10 pages.
International Search Report and Written Opinion for PCT Application No. PCT/US2009/033163, dated Jun. 24, 2009. 7 pages.
International Search Report and Written Opinion for PCT Application No. PCT/US2010/027145, dated Apr. 27, 2010. 10 pages.
International Search Report and Written Opinion for PCT Application No. PCT/US2011/025021, dated Mar. 17, 2011. 5 pages.
Office Action for AU Application No. 2021290424, dated Mar. 6, 2023. 4 pages.
Office Action for CA Application No. 2957083, dated May 5, 2023, 4 pages.
Office Action for CN Application No. 201410230550.2, dated Jan. 25, 2017, 29 pages.
Office Action for CN Application No. 201410230550.2, dated Jul. 24, 2017, 4 pages.
Office Action for CN Application No. 201410230550.2, dated May 23, 2016. 22 pages.
Office Action for CN Application No. 201911107305.1, dated Apr. 7, 2021. 5 pages.
Office Action for CN Application No. 201911107305.1, dated Nov. 13, 2023, 15 pages.
Office Action for EP Application No. 09708428.9, dated Apr. 19, 2021. 10 pages.
Office Action for EP Application No. 10751476.2, dated Oct. 16, 2023. 10 pages.
Office Action for EP Application No. 21158019.6, dated Nov. 23, 2023. 3 pages.
Office Action for JP Application No. 2017-511659, dated Sep. 10, 2019. 7 pages.
Office Action for JP Application No. 2022-032257, dated Feb. 1, 2023. 12 pages.
Office Action for KR Application No. 10-2017-7005509, dated Jun. 25, 2021. 6 pages.
Office Action for KR Application No. 10-2023-7008456, dated Nov. 24, 2023. 11 pages.
Office Action received in CN Application No. 201911107305.1, mailed Oct. 9, 2020. 9 pages.
Office Action received in CN Application No. 202010512125.8, mailed Nov. 16, 2022. 31 pages.
Office Action received in EP Application No. 09708428.9, mailed Nov. 16, 2022. 10 pages.
Office Action received in EP Application No. 10751476.2, dated Dec. 22, 2021. 9 pages.
Office Action received in EP Application No. 15835212.0, dated Sep. 24, 2021. 4 pages.
Office Action received in JP Application No. 2019-507836, mailed Sep. 14, 2021. 6 pages.
Office Action received in KR Application No. 10-2022-7007848, dated Jun. 16, 2022. 6 pages.
Office Action received in U.S. Appl. No. 15/946,461, May 24, 2022. 9 pages.
Office Action received in U.S. Appl. No. 17/560,412, Nov. 30, 2022. 17 pages.
Patent Examination Report 1 for NZ Application No. 729198, dated Jun. 1, 2021. 4 pages.

(56) References Cited

OTHER PUBLICATIONS

Poiseuille flow. (2009). In J. Cullerne (Ed.), Then penguin dictionary of physics (4th ed.). 1 page. Penguin. Credo Reference: https://search.credoreference.com/content/entry/pendphys/poiseuille_flow/0?institutionId=743.
Rejection Decision received in CN Application No. 201911107305.1, dated Nov. 2, 2021. 6 pages.
Search Report received in SG Application No. 10202002657P, mailed Nov. 27, 2023. 7 pages.
Search Report received in SG Application No. 10202002657P, mailed Sep. 1, 2021. 2 pages.
Veltek Associates, Inc., One Touch Command™ SMA™ Microbial Air Sampling Systems Brochure, Revised Dec. 2002, 4 pgs., Malvern, Pennsylvania.
Extended European Search Report issued in App. No. EP24170468, dated Jul. 15, 2024, 7 pages.

\* cited by examiner

Event Log

| Event Time | Message |
|---|---|
| 19-May-14 16:00:32 | admin1 is now now the active user (formerly DEFAULT). |
| 19-May-14 15:54:05 | DEFAULT is now now the active user (formerly admin1). |
| 19-May-14 15:11:30 | admin1 is now now the active user (formerly DEFAULT). |
| 19-May-14 15:11:16 | DEFAULT is now now the active user (formerly op1). |
| 19-May-14 15:10:51 | op1 is now now the active user (formerly DEFAULT). |
| 19-May-14 15:10:33 | DEFAULT is now now the active user (formerly admin1). |
| 19-May-14 14:57:21 | admin 1 is now now the active user (formerly DEFAULT). |
| 19-May-14 14:49:02 | DEFAULT is now now the active user (formerly admin1). |
| 19-May-14 14:45:25 | admin 1 is now now the active user (formerly DEFAULT). |

[ ▽ ] [ △ ]   Reset Flow Alarms   |   Clear Log   |   Silence Alarms

FIG. 9

Security

User Level Security

[ Login ]   [ Logout ]   [ Modify Password ]

[ Current User admin1 ]   [ Administrative Password Reset ]

PROGRAMMABLE LOGIC CONTROLLER-BASED SYSTEM AND USER INTERFACE FOR AIR SAMPLING IN CONTROLLED ENVIRONMENTS

RELATED APPLICATIONS

This application is a continuation of U.S. patent application Ser. No. 17/070,506, filed Oct. 14, 2020, now U.S. Pat. No. 11,971,396, which is a continuation of U.S. patent application Ser. No. 15/946,461, filed Apr. 5, 2018, which is a continuation of U.S. patent application Ser. No. 14/471,848, filed Aug. 28, 2014, now U.S. Pat. No. 9,939,416. The entire contents of these are hereby incorporated by reference.

FIELD OF INVENTION

The present invention relates to devices and methods for monitoring airborne contaminants. In particular, the present invention relates to a programmable logic controller-based system and one or more corresponding operator interface terminals for controlling air sampling in controlled environments.

BACKGROUND OF THE INVENTION

Clean rooms found in manufacturing, research, and other facilities are typically classified into two broad categories based on the static air pressure inside the rooms relative to atmospheric pressure and/or based on the air pressure in spaces adjacent the clean rooms. A positive air pressure room is maintained at an absolute air pressure greater than atmospheric pressure, greater than the air pressure in spaces adjacent the clean room, or both. The positive air pressure in such rooms is provided by pumping filtered and/or conditioned air into the rooms and controlling the flow of air out of the rooms. The adjacent spaces, which may be manufacturing facilities or offices, are typically maintained at or close to atmospheric pressure by heating, ventilation, and air conditioning (HVAC) systems, or by providing an opening to the environment that allows the adjacent spaces to equilibrate with atmospheric pressure. Thus, air flowing from the positive pressure clean room will flow toward the lower pressure in adjacent rooms or to the atmosphere.

When a positive air pressure clean room is breached, air flowing to adjacent spaces or the atmosphere is generally not a problem as long as airborne contaminants present in the clean room do not pose a potential adverse health effect to people in the adjacent spaces. Typically, the air inside clean rooms in which electronics, aerospace hardware, optical systems, military equipment, and defense-related research are manufactured or conducted may not contain airborne gases, vapors, and particulate matter at concentrations that present a safety or health concern to human health or the environment. However, that is not always the case, as other operations within those industries may generate contaminants that are above acceptable levels and, therefore, must be prevented from escaping the clean room without treatment.

A negative air pressure room is maintained at an absolute air pressure that is either less than atmospheric pressure, less than the air pressure in spaces adjacent the clean room, or both. The negative pressure is maintained by pumping air out of the room at a rate faster than that at which filtered and/or conditioned air is pumped into the room. Negative pressure rooms are often used when there is a concern that contaminants in the air in the room may pose a potential health threat to human health in adjacent spaces or the environment.

Notwithstanding the human health and environmental implications, certain types of manufacturing and research operations must be conducted within a positive air pressure clean room to satisfy regulatory requirements and industry-adopted good manufacturing and laboratory quality control standards. For example, state and federal regulations, including those promulgated by the National Institute for Occupational Safety and Health (NIOSH), may necessitate the use of positive or negative pressure clean rooms.

In particular, the U.S. Food & Drug Administration (FDA) requires that pharmaceutical production be performed within the confines of clean rooms that provide for the validation and certification that manufactured batches of pharmaceutical products are being produced in a sanitary environment. Various FDA regulations and standards also specify requirements for air sampling and/or air monitoring equipment to be used inside clean rooms to verify or validate the cleanliness of the facility during certain drug manufacturing activities. The regulations also provide for electronic data recording, accuracy, precision, and record-keeping relating to monitoring the air quality within clean rooms. Similar requirements are imposed on other industries, such as the biotechnology industry.

Current systems for testing and monitoring the air quality in controlled environments include a plurality of sterilizable microbial atriums (SMA) that are connected to a distributed digital control (DDC) controller. An example of an SMA-DDC system includes the SMA-DDC-10 and integrated One Touch Control System produced by Veltek Associates Inc. of Malvern, Pennsylvania. Other systems are shown in U.S. Pat. Nos. 8,169,330; 7,973,668; 7,940,188; 8,188,874; 8,701,980; and U.S. Patent Publication Number 2014-0132415 A1, the disclosures of which are hereby incorporated by reference. Such systems typically include a hardware-based interface that allows users to interface with the air sampling equipment.

As described below, conventional systems require manual control of flow switches to control the mass flow rates of vacuum connections. Additionally, conventional systems require users to monitor and control aspects of the system from limited locations. Additionally, the vacuum pumps of conventional systems may be physically damaged or cause injury if a vacuum connection or air sampling device is obstructed.

SUMMARY OF THE INVENTION

In order to overcome these and other drawbacks of conventional air sampling systems, aspects of exemplary embodiments of the present invention enable automatic regulation of the mass flow rates of each of the vacuum connections based on rates set by an operator. Additionally, aspects of exemplary embodiments of the present invention enable users to monitor and control aspects of the system via network-connected devices. Additionally, aspects of exemplary embodiments of the present invention enable a vacuum pump to be disconnected from power in response to a physical emergency button, a software-based emergency stop button available on network connected devices, and an automatic power disconnection in response to an abnormal mass flow reading that could potentially impact the vacuum pump.

BRIEF DESCRIPTION OF THE DRAWINGS

For the purpose of illustration, there are shown in the drawings certain embodiments of the present invention. In the drawings, like numerals indicate like elements throughout. It should be understood that the invention is not limited to the precise arrangements, dimensions, and instruments shown. In the drawings.

DETAILED DESCRIPTION OF THE INVENTION

The present invention will be explained in terms of exemplary embodiments. This specification discloses one or more embodiments that incorporate the features of this invention. The disclosure herein will provide examples of embodiments, including examples of data analysis from which those skilled in the art will appreciate various novel approaches and features developed by the inventors. These various novel approaches and features, as they may appear herein, may be used individually, or in combination with each other as desired.

Figure 1:
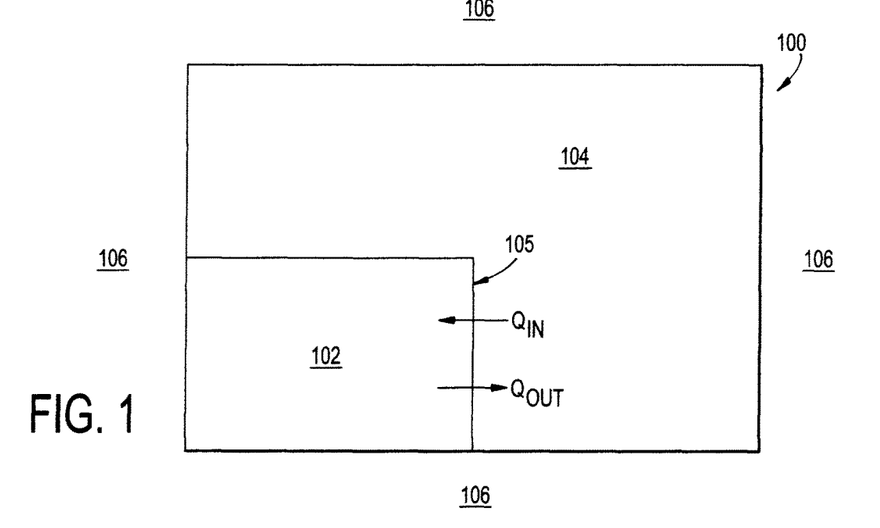
FIG. 1 is a schematic diagram of an exemplary facility having a clean room therein, in accordance with an exemplary embodiment of the present invention.

Turning first to FIG. 1, shown therein is a schematic of an exemplary facility 100 having one or more clean rooms 102 therein, in accordance with an exemplary embodiment of the present invention. The clean room 102 is surrounded by an adjacent space 104 and the outdoor atmosphere 106. The adjacent space 104 may be one or more rooms within the same facility 100 in which the clean room 102 is located and that adjoin the clean room 102, such as, for example, a separate manufacturing room, another clean room, a finish and fill room, a research laboratory, offices, etc. The clean room 102 and adjacent space 104 are separated by a divider, such as a wall 105.

The clean room 102 in the exemplary facility 100 is capable of being maintained at an air pressure $P_1$ that is less than or greater than the air pressure $P_2$ of the adjacent space 104 and atmospheric air pressure $P_{ATM}$ of the outdoor atmosphere 106. That is accomplished by an HVAC system (not shown) that causes conditioned and filtered air to be pumped into the clean room 102 at a controlled flow rate $Q_{IN}$ as depicted in FIG. 1. Air inside the clean room 102 that is pumped out of or otherwise flows out of the clean room 102 is represented by $Q_{OUT}$. When the difference between $Q_{IN}$ and $Q_{OUT}$ (i.e., $Q_{IN}-Q_{OUT}$) is greater than zero, a positive pressure will be maintained in the clean room 102. And, when the difference between $Q_{IN}$ and $Q_{OUT}$ is less than zero, a negative pressure will be maintained in the clean room 102.

Figure 2:
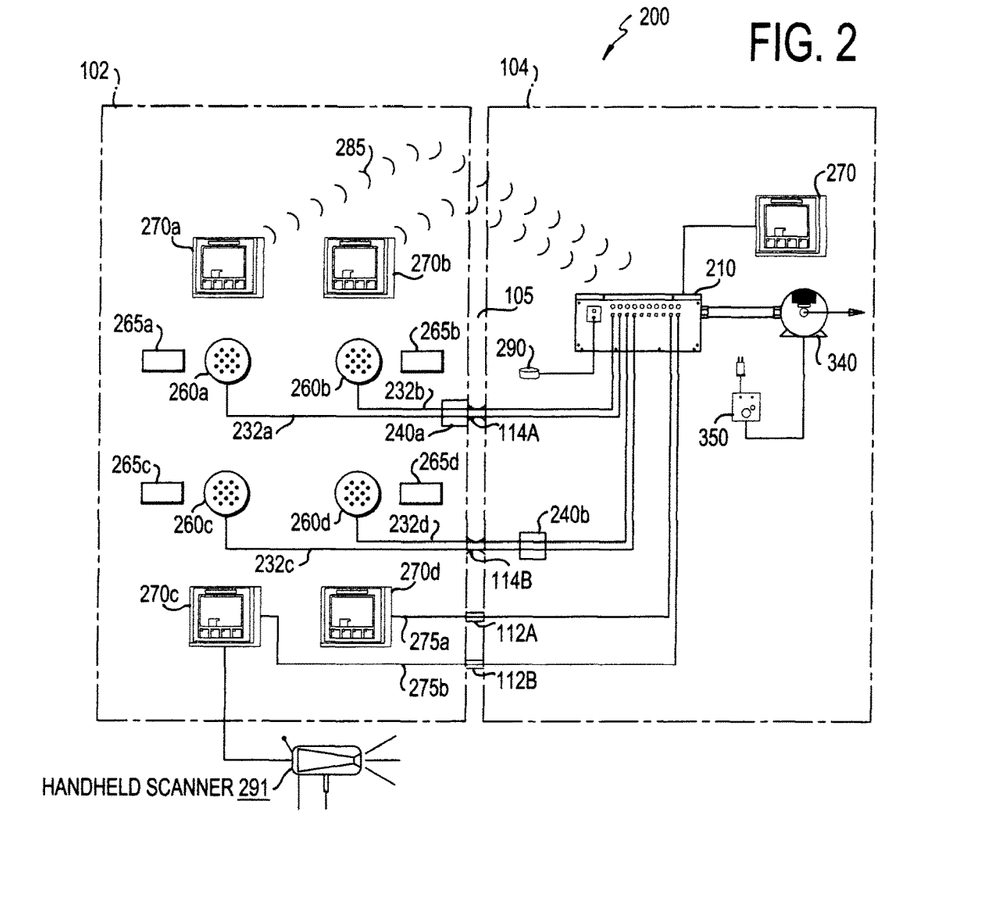
FIG. 2 is a schematic diagram of a tracking/logging and air sampling/monitoring system for use in the clean room of FIG. 1 that includes a PLC-based controller and one or more associated touch panel displays, in accordance with an exemplary embodiment of the present invention.

Turning now to FIG. 2, shown therein is a schematic diagram of an air sampling/monitoring system 200, in accordance with an exemplary embodiment of the present invention. The system 200 generally includes a controller 210, flow centers 240, air sampling devices 260, operator interface terminals 270, a vacuum pump 340 and a contactor 350. The controller 210, the flow centers 240, and the operator interface terminals 270 may include, processors, displays, wireless devices, and memory to operate in accordance with the invention. As described below, the controller 210, flow centers 240, air sampling devices 260, operator interface terminals 270 may each be associated with its own sensor 291 or a shared sensor 291.

The system 200 is configured for use in tracking and logging data obtained from the process of air sampling through the air sampling devices 260. During air sampling, air from the clean room 102 is drawn through the air sampling devices 260 of the system 200 to collect contaminants present in the air of the clean room 102. The data acquired about the air sampling devices 260 is used to monitor and gather airborne particle count and other parameter levels in the clean room 102 in order to maintain the integrity of experiments or production processes therein.

One or more flow centers 240 are provided to monitor and control the flow of air through one or more vacuum connections 232. The flow centers 240 may be free standing or wall mounted within the clean room 102, outside the clean room 102, or in multiple clean rooms 102. (As illustrated in FIG. 2, for example, flow center 240a is inside the clean room 102 and the flow center 240b is outside the clean room 102.) The flow centers 240 may include modular ports, such as the modular ports described and illustrated in the '330 Patent, where each of such ports may be connected to a vacuum connection 232. Using these ports, the flow centers 240 can be configured to draw in air from the air sampling devices 260 and to provide for the air sampling performed by the air sampling devices 260. The vacuum connections 232 may be connected across the wall 105 via a wall-mounted quick disconnect outlets 114, where the outlets and are located on the wall 105 in between the clean room 102 and the adjacent space 104.

A plurality of air sampling devices 260 may be co-located together in the clean room 102 or in multiple clean rooms. The air sampling devices 260 may be any known air sampling device for collecting a volume of air. An example of an air sampling device suitable for use as the air sampling devices 260 is described in the '330 Patent and/or U.S. Pat. No. 8,474,335, the contents of which are incorporated herein by reference.

The subjects 265 are located at various sites within the clean room 102. The subjects 265 may be equipment, personnel, etc. The air sampling devices 260 may be positioned, for instance, adjacent to one or more of the subjects 265 to collect the air surrounding respective subjects 265, i.e., to draw air over the subjects 265 during air sampling, so that contaminants in the air of the clean room 102 at sites of interest are collected by the air sampling devices 260. The sensors 291 may device configured to identify the subjects 265. For example, the sensors may include cameras, radio frequency identification (RFID) readers, barcode scanners, etc The controller 210 communicates data and commands for monitoring and controlling the system 200 in real time (or near real time) and logging the data and commands in a database 290 maintained by the controller 210. The controller 210 may be any suitable computing device, such as a server. The controller 210 may be freestanding or wall mounted in a rack-style chassis. The database 290 may be any computer-readable storage medium and may be co-located with the controller 210 or remotely located. (The controller 210 may include the same or similar features as "controllers" or "control centers" described in documents incorporated in this description by reference.)

The operator interface terminals 270 communicate data and commands for monitoring and controlling the system 200. Each of the operator interface terminals 270 may be any suitable computing device, such as a desktop computer, notebook computer, touch screen computer, an identifying device (such as a camera, a barcode scanner, an RFID reader, a fingerprint reader, etc.), etc. Each operator interface terminal 270 may include a monitor, a speaker, a touch screen and/or a keyboard. The operator interface terminals 270 may be wall-mounted, desktop, portable, or a combination. Operator interface terminals 270 may be located throughout the system 200. For example, operator interface terminals 270 may be co-located with the controller 210, the flow centers 240, the air sampling devices 260, etc. An operator interface terminal 270 that is co-located with another hardware component (such as the controller 210, the flow centers 240) may communicate with the hardware component directly or via a network connection. As described below, each operator interface terminal 270 includes a graphical user interface (GUI) that can be readily accessed by the users to monitor and control the system 200.

The exemplary embodiment of the system 200 illustrated in FIG. 2 illustrates one clean room 102, two flow centers 240*a-b* and four vacuum connections 232*a*-232*d*, each of which corresponds to a respective one of four air sampling devices 260*a*-260*d*. It is to be understood that the number of clean rooms 102, flow centers 240, vacuum connections 232, air sampling devices 260, and sensors 291 is not limited thereto. That is, the system 200 is linearly scalable to substantially any number, n, of clean rooms 102*a*-102*n*, flow centers 240*a*-240*n*, vacuum connections 232*a*-232*n*, air sampling devices 260*a*-260*n*, subjects 265*a*-265*n*, and operator interface terminals 270*a*-270*n*.

The controller 210, the flow centers 240, and the operator interface terminals 270 communicate with one another in any suitable manner. For example, the operator interface terminals 270 and the flow centers 240 may have network addresses, and the controller 210 may communicate with the flow centers 240 and the operator interface terminals 270 by use of those network addresses via a common connection (e.g. an Ethernet network or wireless local area network (LAN)). In the exemplary embodiment illustrated in FIG. 2, the flow centers 240*a* and 240*b* and the operator interface terminals 270*c* and 270*b* communicate with the controller 210 via wired networking connections 275 while the operator interface terminals 270*a* and 270*b* communicate with the control panel 210 via wireless signals 285. The wired networking connections 275 may pass from the adjacent space 104 into the clean room 102, for example, via channels 112. The controller 210, the flow centers 240, and the operator interface terminals 270 may communicate via networking communication and/or raw electronic signals.

In one exemplary scenario, a first operator interface terminal such as first operator interface terminal 270*a* may be located near a first air sampling device such as air sampling device 260*a* and away from a second air sampling device such as air sampling device 260*b*. By interacting with the graphical user interface presented by the first operator interface terminal 270*a*, the user may cause a signal to be sent to the controller 210 and/or the flow center 240*a* for thereby controlling or monitoring the second air sampling device 260*b*. Thus, any air sampling device 260*a-d* may be controlled or monitored using any operator interface terminal 270*a-d* irrespective of where they are located.

In another exemplary scenario, an alarm may be generated by a first operator interface terminal 260*a* and a notification of the alarm may be presented to one or more of the operator interface terminal 270*a-d* irrespective of their locations. For example, in the exemplary configuration shown in FIG. 2, an alarm generated by the operator interface terminal 260*a* may be detected by the controller 210 and then information associated with the alarm may be relayed to one or more of the remotely-located operator interface terminal 270*b-d*, instead of or in addition to the adjacent operator interface terminal 270*a*. In this way, important alarm information may be automatically presented to the location(s) where users are located when the alarm is detected rather than being presented only at the location of the alarm, where users may or may not be located. It will be recognized, however, that the operator interface terminal 270 can directly communicate with one another, such as to de-activate an alarm signal.

The programmable logic controller (PLC) may be a digital computer used for automation of electromechanical processes, including control of machinery, such as the sterilizable microbial atriums (SMAs) described herein. Unlike general-purpose computers, the PLC may be designed for multiple inputs and output arrangements, extended temperature ranges, immunity to electrical noise, and resistance to vibration and impact. The PLC may be programmed using application software executed on separate general purpose computers. Such a computer may be connected to the PLC through Ethernet, RS-232, RS-485, RS-422, or other suitable communications cabling. Generally, the programming software provides functions for debugging and troubleshooting the PLC software, for example, by highlighting portions of the logic to show current status during operation or via simulation. The software can upload and download the PLC program for backup and restoration purposes. In some PLC embodiments, the program is transferred from a personal computer to the PLC through a programming board which writes the program into a removable memory chip such as an SD card, an EEPROM, an EPROM, etc. PLCs may be used to interact with users for the purpose of configuration, alarm reporting or everyday control. A human-machine interface (HMI) is employed for this purpose. HMIs are also referred to as a human-computer interface (HCI), a man-machine interface (MMI) and a graphical user interface (GUI) displayed on a human-machine interface. A simple system may use buttons and lights to interact with the user. Text displays are available as well as graphical touch screens.

The system 200 may also be configured to interface with a customer's existing hardware. For example, the controller 210 may send and receive data to and from a customer's existing industrial control systems, such supervisory control and data acquisition (SCADA) systems and/or data collection systems (DCS). A typical SCADA system is a desktop or server-based computer running a SCADA application. The controller 210 may also contain power supplies for remote systems such as the flow centers 240, the distributed PLCs 310 (discussed below), and the operator interface terminals 270.

Figure 3:
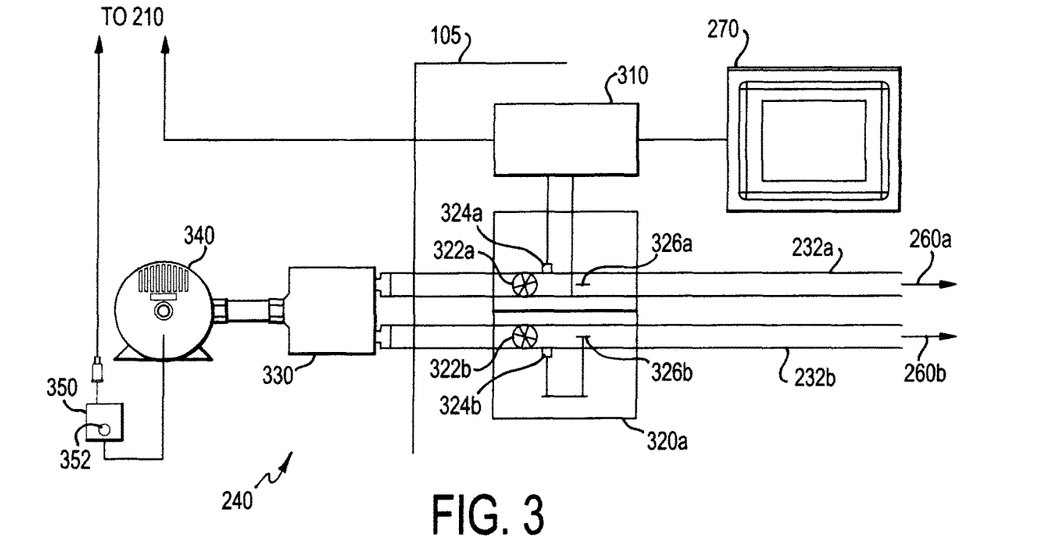
FIG. 3 is a schematic diagram of a flow center according to an exemplary embodiment of the present invention.

FIG. 3 is an overview of a flow center 240 according to an exemplary embodiment of the present invention. The flow center 240 includes a distributed PLC 310, an operator interface terminal 270, and one or more mass flow controllers 320. Each of the mass flow controllers 320 includes a flow control valve 322, an actuator 324, and a flow sensor 326. Each of the vacuum connections 232 may be in flow communication with a manifold 330 and a vacuum pump 340. The vacuum pump 340 and/or the manifold 330 may be located in interstitial space outside the clean room 102.

The flow center 240 includes one or more vacuum connections 232, each of which are in flow communication with one of the air sampling devices 260. The flow center 240 is configured to draw air from each of the air sampling devices 260 through the vacuum connections 232. The air drawn from through the vacuum connections 232 is combined by the manifold 330 and exhausted to the vacuum pump 340. The vacuum pump 340 may be in flow communication with either the flow center 240 or the controller 210. (As illustrated in FIG. 2, for example, the vacuum line of the vacuum pump 340 is split by the controller 210 and regulated by the flow centers 240.

The flow center 240 is configured to independently monitor and adjust the flow rate of each of the vacuum connections 232 while sending and receiving signals from the distributed PLC 310 to each of the mass flow controllers 320. Each of the mass flow controllers 320 includes a flow control valve 322 configured to control the flow rate through the vacuum connection 232 by positioning the valve. Each of the mass flow controllers 320 also includes an actuator 324 configured to outputs electrical signals to open or close the flow control valve 322 based on electrical signal received from the distributed PLC 310. Each of the mass flow controllers 320 also includes a flow sensor 326 configured to output an electrical signal to the distributed PLC 310 based on the rate of flow through the vacuum connection.

The flow sensor 326 may be any suitable device configured to output an electrical signal proportional to the mass flow rate of air passing through the vacuum connection 232. For example, the flow sensor 326 may be a capillary configured to draw in a small volume of air, sense an increase in temperature proportional to the flow rate, translate a change in resistance (due to the increase in temperature) into an electrical voltage, and output an electrical current to the distributed PLC 310. The distributed PLC 310 includes software configured to scale the electrical signal to the appropriate engineering units.

The distributed PLC 310 may communicate with the controller 210 via any suitable method. For example, the distributed PLC 310 may communicate with the controller 210 using common industrial protocol (or other protocols) over a wireless or wired network connection. The distributed PLC 310 is configured to monitor the flow rate of each of the vacuum connections 232 in the flow center 240 based on the flow rate measurements received from each flow sensor 326 of each mass flow controller 320 and output the flow rate measurements to the controller 210 or other networked devices.

The distributed PLC 310 is also configured to control the flow rate of each of the vacuum connections 232 in the flow center 240 by outputting electrical signals to actuator 324 of the mass flow controller 320. For example, the flow center 240 may be configured such that the distributed PLC 310 compares a desired flow rate (or "setpoint") set by the user with the actual measured flow rate received from the flow sensor 326 and determines the difference ("error") between the setpoint and the measured flow rate. Depending on whether the error is positive (i.e., the measured flow rate is greater than the setpoint) or negative (i.e., the setpoint is greater than the measured flow rate), the distributed PLC 310 outputs electrical signals to the actuator 324 to either open or close the flow control valve 322. The electrical signals output to the actuator 324 may be proportional to the size of the error. For example, if the error is small, the distributed PLC 310 will output an electrical signal to the actuator 324 to open or close the valve 324 by a small amount. If the error is large, the distributed PLC 310 will output an electrical signal to the actuator 324 to open or close the valve 324 by a larger amount. Accordingly, the change in position (i.e. magnitude) of the flow control valve 322 may be proportional to the size of the error. Additionally, the rate at which the flow control valve 322 changes may be proportional to how fast the mass flow rate measurement changes. This is known as proportional-integral-derivative control or PID control.

Using conventional systems, the mass flow rates of each of the vacuum connections 232 must be manually controlled by manually adjusting a flow switch on each line to change the position of each valve. Because some or all of the vacuum connections 232 are in flow communication (for example, via a manifold 330), adjusting one flow switch for one vacuum connection 232 may inadvertently affect the mass flow rates of other vacuum connections 232. Accordingly, conventional systems required multiple flow switches to be adjusted to adjust the mass flow rate of one vacuum connection 232 and maintain a constant mass flow rate of other vacuum connections 232. Additionally, multiple flow switches of a conventional system must be adjusted if an additional vacuum connection 232 is active or if an air sampling device 260 is disturbed. The system 200 overcomes this drawback of conventional systems by automatically adjusting the mass flow rates of each of the vacuum connections 232 to the individual rates set by an operator.

Each of the flow centers 240 may include an operator interface terminal 270, including a graphical user interface (GUI) that can be readily accessed by the users to monitor and control the mass flow rates of each of the vacuum connections 232. Additionally, each distributed PLC 310 is network connected to the controller 210 and other industrial and enterprise devices via proprietary and open-source communications protocols. Because the distributed PLCs 310 are network connected, the mass flow rates of each of the vacuum connections 232 may also be monitored and/or controlled from the controller 210, other operator interface terminals 270 (i.e., terminals that are not co-located with the flow center), and/or an office computer, industrial workstation, mobile device, or any other internet-enabled computing device via a web browser. The industrial control systems may include supervisory control and data acquisition (SCADA) systems, data collection systems (DCS), human machine interfaces (HMI), manufacturing execution systems (MES), plant-monitoring systems (PMS), and similar systems. The controller 210, the distributed PLCs 310, the operator interface terminal 270, and the industrial control systems may be connected via a network as described above. Each of the network-connected systems may be remotely accessed via the internet.

If one or more of the air sampling devices 260 or vacuum connections 232 becomes obstructed, the corresponding vacuum pump 340 may overheat or suffer physical damage. A damaged vacuum pump 340 has the potential to threaten the safety of personnel by causing a fire or projecting broken pieces. In order to minimize this potential safety risk, each of the vacuum pumps 340 includes a contactor 350 to deliver and control electrical power to the respective vacuum pump 340. The system 200 may be configured such that the contactor 350 automatically disconnects power from the vacuum pump 340 if a flow rate is not detected by one or more of the flow sensors 326. Additionally, each of the contactors 350 may include an emergency stop button 352 that, when actuated, interrupts all electrical power connections to the vacuum pump 350 and outputs an alarm signal to the distributed PLC 310, the controller 210, and/or other network-connected devices. In addition to the emergency stop button 352, each of the contactors 350 may be controlled by a software-based emergency stop button included in the graphical user interface (GUI) of the operator interface terminal 270 or other network connected devices. The GUI may also output an indication if an emergency is detected by any network-connected device or if one of the emergency stop buttons 352 or software-based stop buttons is selected on another network-connected device.

The system 200 is also configured to automatically disconnect the power supplied to a vacuum pump 350 in response to a determination that any one of the vacuum connections 232 in flow communication with the vacuum pump 350 is experiencing an abnormally low mass flow rate (e.g., 0). Whereas conventional systems would shut down a vacuum pump only if all sample points were manually aborted, the system 200 provides additional protection against a vacuum pump 350 being damaged by an obstructed air sampling device 260 or vacuum connection 232.

In addition to the normal operation described above, the system 200 may also be configured enter an auxiliary mode (or Isolator Mode) wherein the system 200 is configured to purge the vacuum connections 232 and the air sampling devices 260. An exemplary purging process is described in U.S. Pat. No. 8,169,330 (which is incorporated herein by reference). The system may include one or more purge pumps (not shown) in flow communication with the vacuum connections 232. Each of the vacuum connections 232 may include isolator equipment (not shown) configured such that air from the air sampling devices 260 bypasses the flow centers 240 and instead flows to the purge pumps. The isolator equipment may be co-located with or external to the flow centers 240. The isolator equipment and the purge pump may be connected via a network as described above.

As described above, the system 200 may be configured such that a graphical user interface (GUI) is available on any of the operator interface terminals 270 or other network-connected devices. The GUI displays information regarding each of the ports (e.g., air sampling devices 260) and vacuum pumps 340 received from the controller 210, flow centers 240, or other network connected devices. The system 200 may be configured such that a user may control any of the ports (e.g., air sampling devices 260) or vacuum pumps 340 throughout the system via the GUI. Referring to FIGS. 2 and 3, for example, a user may adjust the air sampling rate of the air sampling device 260b from the operator interface terminal 270a (which may be located next to the air sampling device 260a) by inputting a setpoint for the air sampling device 260b via the GUI. In response to the user input, the system 200 may send a signal from the operator interface terminal 270a to the distributed PLC 310 associated with the vacuum connection 232b in flow communication with the air sampling device 260b (for example, via a wireless signal 285 to the controller 210 and via a wired or wireless signal to the distributed PLC 310 of the flow center 240a). The distributed PLC 310 of the flow center 240a sends a signal to actuator 324b to adjust the flow control valve 322b and receives a signal from the flow sensor 324b regarding the mass flow rate of the vacuum connection 322b. The distributed PLC 310 adjusts the flow control valve 322b in response to signals from the flow sensor 324b as described above until the mass flow rate of the vacuum connection 232b corresponds to (e.g., is within a predetermined margin of error of) the user input. Because the vacuum connection 232b is also in flow communication with the vacuum connection 232a via the manifold 330, adjusting the flow rate of the vacuum connection 232b as described above may indirectly affect the flow rate of the vacuum connection 232a. Accordingly, the distributed PLC 310 may receive updated measurements of the mass flow rate of the vacuum connection 232a from the flow sensor 326a and send signals to the actuator 324a to compensate for the indirect change in the mass flow rate of the vacuum connection 232a until the mass flow rate of the vacuum connection 232a corresponds to the previously determined setpoint for the air sampling device 260a.

Figure 4:
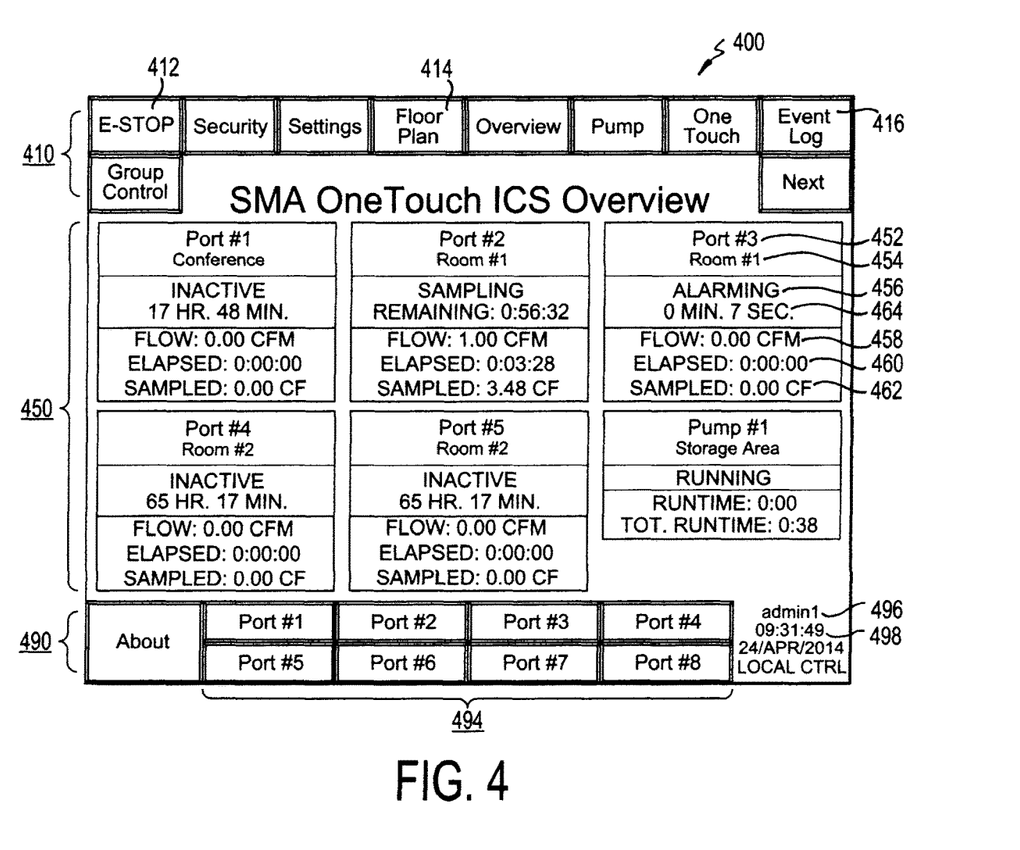
FIG. 4 illustrates a system overview screen of a graphical user interface (GUI) according to an exemplary embodiment of the present invention.

FIG. 4 illustrates an overview screen 400 of the GUI according to an exemplary embodiment of the present invention. The overview screen 400 may include a top toolbar 410, including the software-based emergency stop button 412 to issue a system halt request as described above. Users can use navigation buttons on the top toolbar 410 to navigate to screens to log in or log out of their account, access system settings, monitor sample points (for example, each of the flow sensors 326), monitor the vacuum pumps 340, view a log of system activity, and navigate back to the overview screen 400. The overview screen 400 includes an overview area 450, including operational parameters regarding one or more ports. For example, the overview area 450 may include the name 452, location 454, status 456, current flow rate 458, sample duration 460, and the volume sampled 462. During sampling, the overview area 450 may include the volume remaining and/or the time remaining. The overview area 450 may also include the inactive time 464 (i.e., how long sampling has been inactive) when the port is inactive, the time remaining during Isolator mode, the volume or time remaining when sampling, and/or the alarm duration if the sample is alarming. The overview screen 400 may also include a lower toolbar 490, including an about button 492 that navigates to a screen which describes the system 200, port buttons 494 that navigate to screens to monitor and control each port, the username 496, and the time/date 498.

Each port corresponds to one of the respective air sampling devices 260. The operational parameters of each port are set by the user via the GUI and/or measured by the flow sensor 326 of the flow controller 320 corresponding to the vacuum connection 232 in flow communication with the corresponding air sampling device 260.

The system 200 samples the subjects 265 at a desired flow rate. The system 200 may be adjustably configured to automatically conclude after a preset time elapses and/or after a preset volume is sampled. The GUI enables a user to adjust the preset time, adjust the preset volume, and configure the system to automatically conclude after the preset time, preset volume, or both. If the flow rate deviates from the desired flow rate beyond acceptable alarm limits, the system 200 outputs an alarm to network-connected devices.

The GUI enables users to stop sampling in response to the alarm. The GUI also enables the user to set and/or adjust the desired flow rate and the acceptable limits. The GUI may be configured to display the flow rate in either cubic feet per minute (CFM), liters per minute (LPM), or cubic meters per minute (CMM). The GUI may be configured to display units of volume in cubic feet (CF), liters (L), or cubic meters (CM). The system 200 may be configured to enter Isolator Mode as described above. The system 200 may be configured to remain in Isolator Mode until manually aborted or until a predetermined time has elapsed. The GUI enables the user to manually abort the Isolator Mode or set or adjust the predetermined time for Isolator Mode to automatically conclude.

Figure 5:
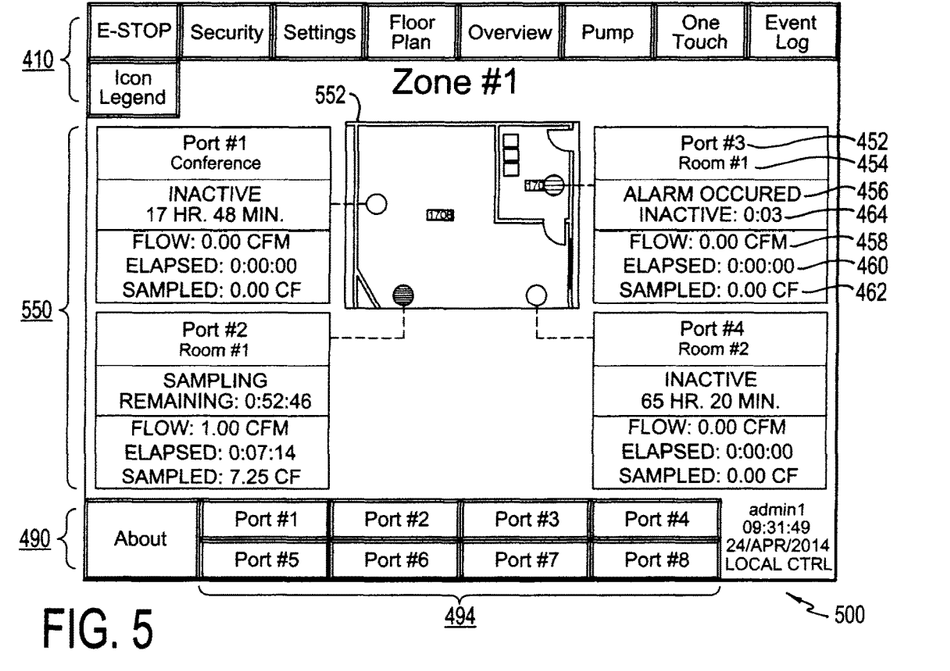
FIG. 5 illustrates a floor plan screen of the GUI according to an exemplary embodiment of the present invention.

The top toolbar 410 may also include a floor plan button 414 that navigates to floor plan screens 500 of the GUI. FIG. 5 illustrates one of the floor plan screens 500 according to an exemplary embodiment of the present invention. The floor plan screens 500 may include the top toolbar 410 and lower toolbar 490 described above. Each of the floor plan screens 500 may also include a zone floor plan area 550 that includes an overlay of operational parameters onto an image of an architectural drawing. In the exemplary embodiment illustrated in FIG. 5, the zone floor plan area 550 includes an architectural drawing 552 of a portion of the system 200 identified as Zone #1, which includes ports 1 through 3 in room 170. The zone floor plan area 550 may include operational parameters regarding each port, for example, the name 452, location 454, status 456, current flow rate 458, sample duration 460, volume sampled 462, and either volume remaining or time remaining 464

Figure 6:
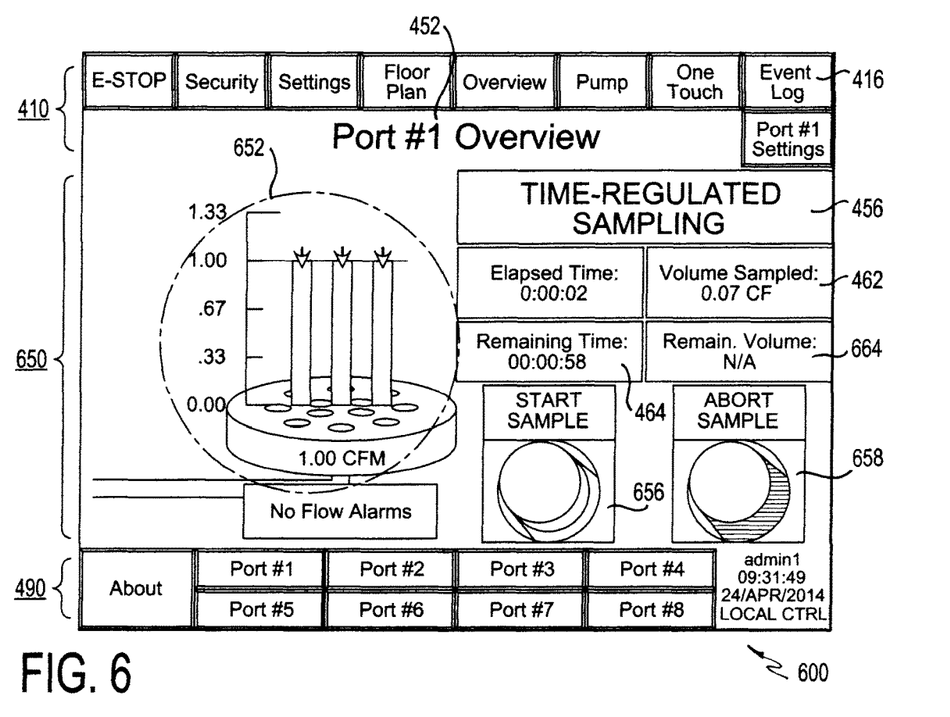
FIG. 6 illustrates a port overview screen of the GUI according to an exemplary embodiment of the present invention.

Selecting one of the port buttons 494 navigates to a port screen 600 corresponding to the port identified by the port button 494. FIG. 6 illustrates one of the port screens 600 according to an exemplary embodiment of the present invention. The port screens 600 may include the toolbars 410 and 490 described above. The port screen 600 may also include a port area 650 that provides an overview of one of the ports. In the exemplary embodiment illustrated in FIG. 6, the port area 650 includes the process information of port #2. The process information may include the name 452, location 454, status 456, current flow rate 458, sample duration 460, volume sampled 462 and either volume remaining 664 or time remaining 464 (when applicable) of the selected port. Additionally, the port area 650 may include a graphical representation 652 of the flow rate of the selected port. Alarms 654 may be displayed as they occur and colors may change to indicate abnormal conditions. The port area 650 may also include an initiation button 656 configured to initiate the sampling process and/or an abort button 658 configured to abort the sampling process. Users may also navigate to the settings screen and modify various process control settings, such as the desired flow rate and the preset time and/or preset volume sampled before sampling is concluded.

Figure 7:
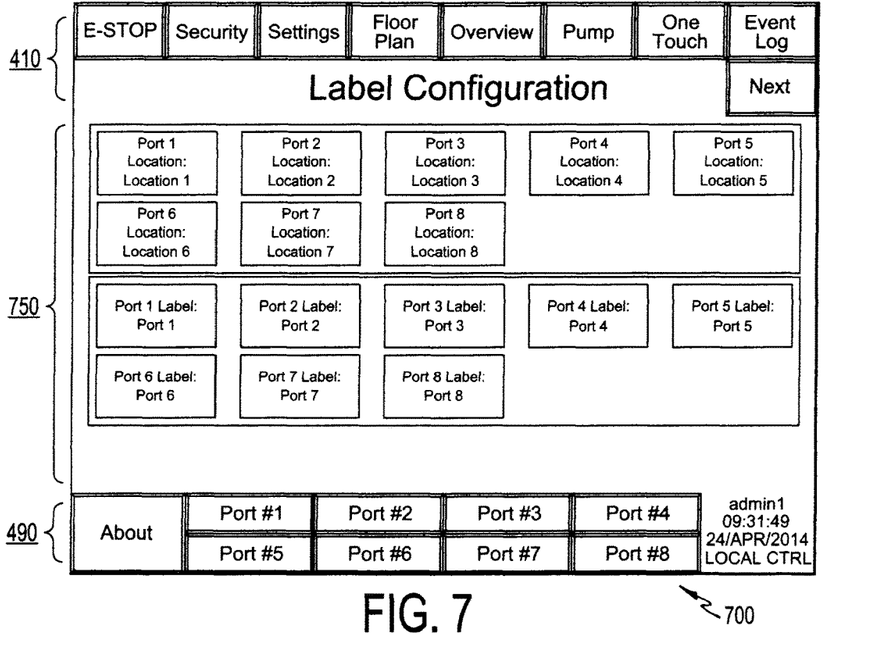
FIG. 7 illustrates a labeling screen of the GUI according to an exemplary embodiment of the present invention.

FIG. 7 illustrates a labeling screen 700 according to an exemplary embodiment of the present invention. The labeling screen 700 may include the toolbars 410 and 490 described above. The labeling screen 700 may also include a labeling area 750 wherein a user may label each of the ports and/or the location of each of the ports.

Figure 8:
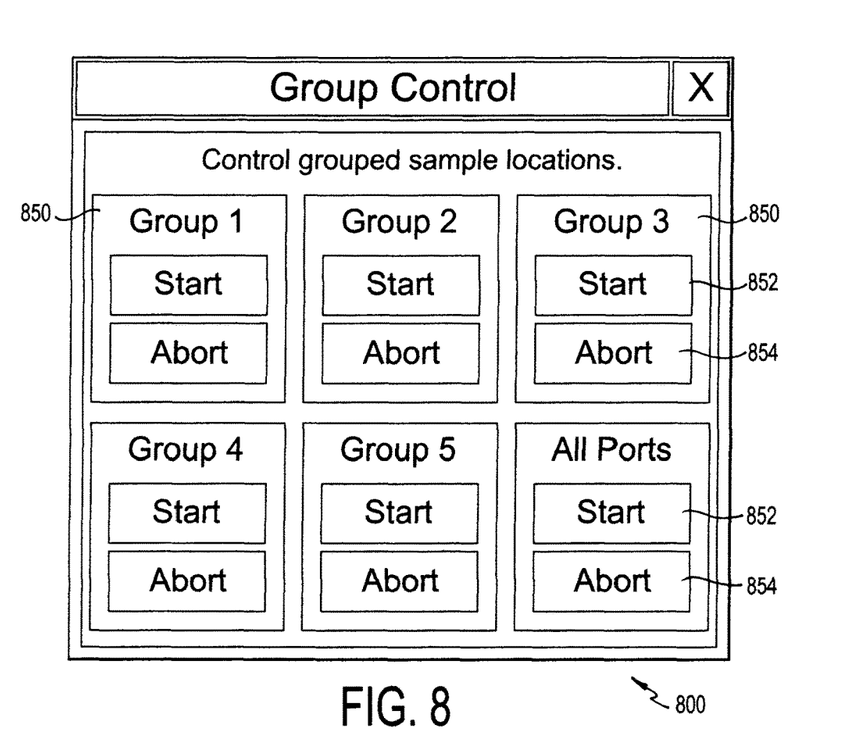
FIG. 8 illustrates a group control screen of the GUI according to an exemplary embodiment of the present invention.

The system 200 is configured such that individual ports may be controlled as a group. FIG. 8 illustrates a group control screen 800 according to an exemplary embodiment of the present invention. The group control screen 800 includes include group areas 850 to control groups of ports (for example, multiple or all ports in a single room or section of a room) with a single user operation. The group control screen 800 may also include an all ports area 860. Each group area 850 may include a start button 852 and an abort button 854 configured to initiate and abort the air sampling process in each of the ports included in the group.

Figure 9:
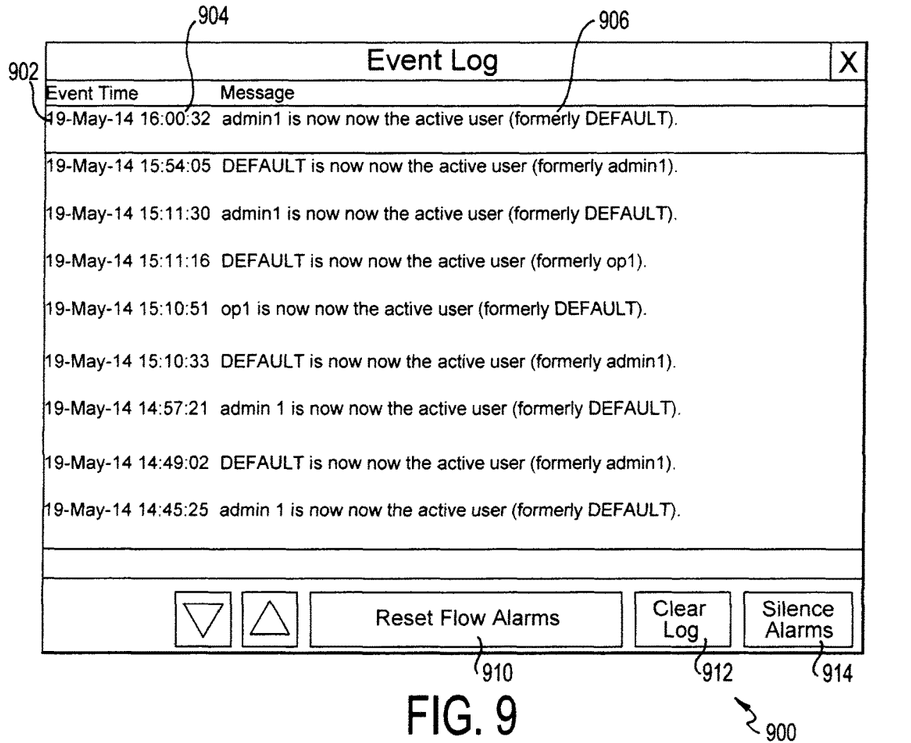
FIG. 9 illustrates an event log screen of the GUI according to an exemplary embodiment of the present invention.

The system 200 is configured to record the time of each system event and the user of that commanded each event. FIG. 9 illustrates an event log screen 900 according to an exemplary embodiment of the present invention. The event log screen 900 may be accessible via the event log button 416 of the top toolbar 410 illustrated in FIG. 4. The event log screen 900 includes the date 902, time 904, and description 906 of each system event. The system 200 may also be configured such that event logs may be printed, exported, and/or viewable on external systems. The event log screen 900 may also include a reset alarms button 910 configured to reset alarms, a clear log button 912 configured to clear the event log, and a silence horn button 914 configured to silence an audible alarm.

The system 200 may be calibrated in the field (for example, using an external flow meter). Accordingly, the system 200 may include a Maintenance Mode in which the system is configured to override the operational flow rate setpoint. In Maintenance Mode, the system 200 may be configured to disable alarming functions. Additionally, the system 200 enables a user to set a reminder for maintenance of the vacuum pump 340. The system 200 may be configured to enable the user to set a maintenance reminder threshold, such as a specific date, a number of days since the vacuum pump 340 was previously maintained, and/or a number of hours that the vacuum pump 340 has been operating since the vacuum pump 340 was previously maintained. The system 200 may be configured to output a reminder to the user when the maintenance reminder threshold is near or has passed.

Figure 10:
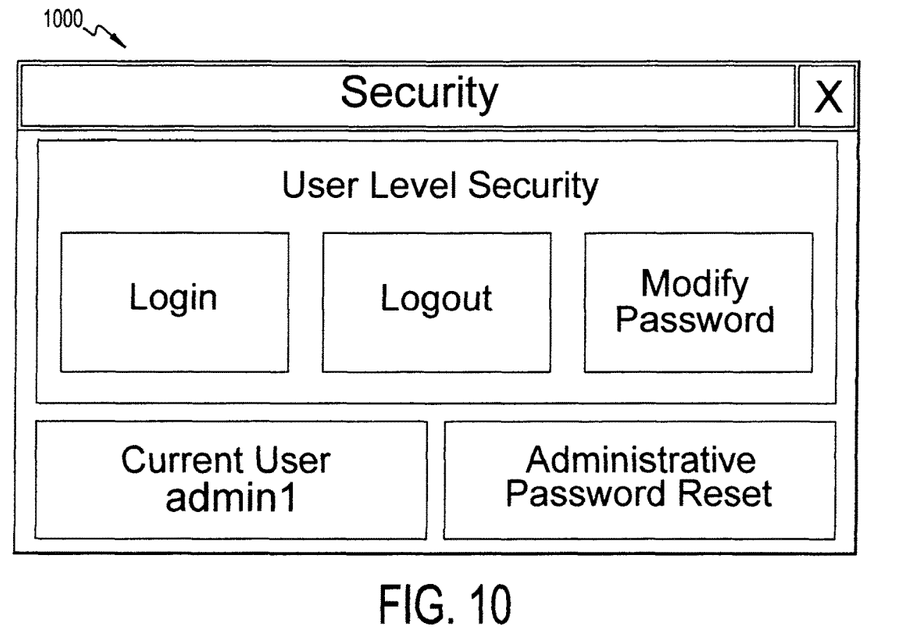
FIG. 10 illustrates a security screen of the GUI according to an exemplary embodiment of the present invention.

The system 200 is configured to authenticate users based on user accounts, each with a username and password, to prevent unapproved interaction with the system. FIG. 10 illustrates a security screen 1000 according to an exemplary embodiment of the present invention. The security screen 1000 enables a user access a user account using a username and password. Different types of user accounts have different access to functionality. For example, a "guest user" account is permitted to view the status of the system but is not permitted to issue commands; an "operator" account is permitted to start and stop the system; an "engineering" account is permitted to configure certain settings; and an "administrator" account is permitted to configure user account settings.

Figure 11:
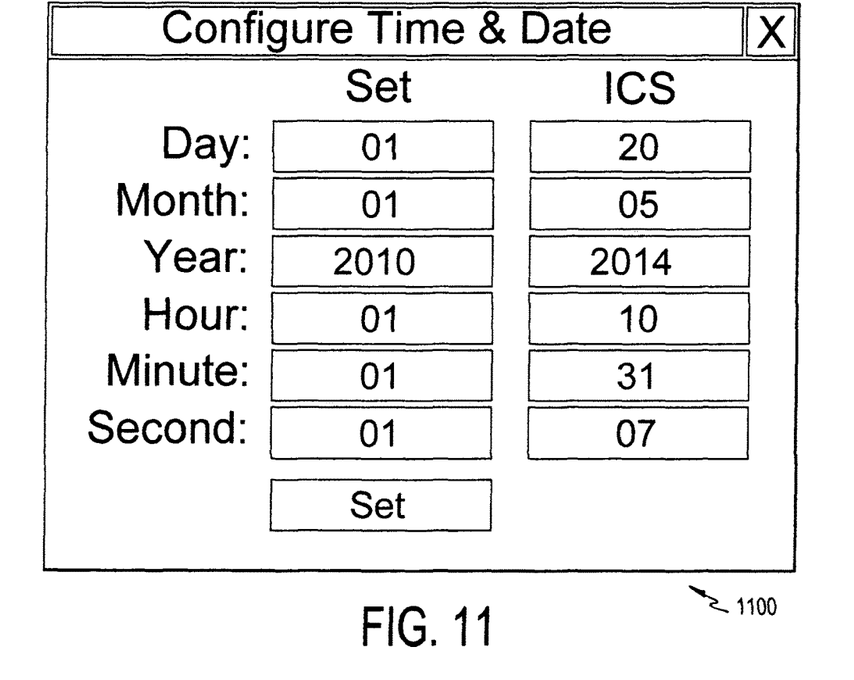
FIG. 11 illustrates a time and date screen of the GUI according to an exemplary embodiment of the present invention.

The GUI also enables a user to synchronize the date and time across the system 200, including the time/date of the controller 210, the operator terminals 270, etc. FIG. 11 illustrates a time and date screen 1100 according to an exemplary embodiment of the present invention.

Figure 12:
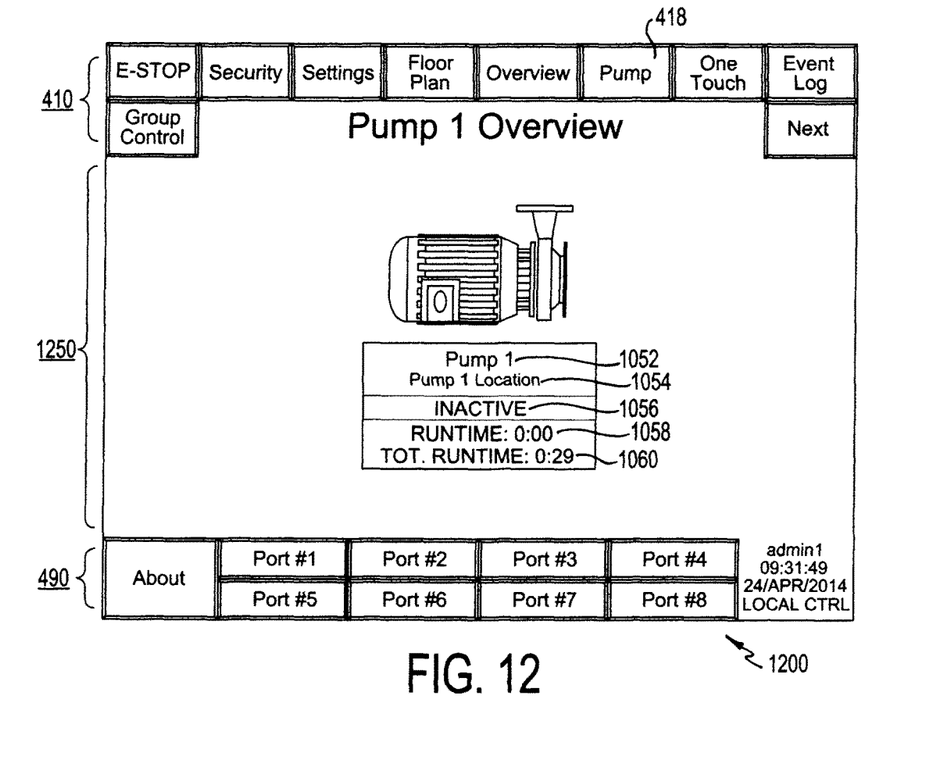
FIG. 12 illustrates a pump overview screen of the GUI according to an exemplary embodiment of the present invention.

The GUI also enables a user to monitor each individual vacuum pump 340. FIG. 12 illustrates a pump overview screen 1200 according to an exemplary embodiment of the present invention. The pump over screen 1200 may include the toolbars 410 and 419, and may be accessible to a user by selecting the pump button 418 of the top toolbar 410. The GUI may include a pump overview screen 1200 for each vacuum pump 340 installed in the system 200. In the exemplary embodiment illustrated in FIG. 13, the pump overview screen 1200 includes a pump overview section 1250 illustrating the process information of Pump #1. The process information may include the name 1052, location 1054, status 1056 (active or inactive), current runtime 1058 and total runtime 1058. The current run time 1058 is the time since the vacuum pump 340 was shut off. The total runtime 1058 is the sum of all runtime and may be reset by an operator.

The system 200 may also be configured to output alarm notices if the system 200 experiences an alarm system while sampling or if an abnormal condition occurs. The system 200 may output alarm notices to the operator interface terminals 270 or other network-connected devices via the GUI. An alarm signal may be output in response to abnormal flow conditions, loss of system flow, or if an emergency stop button 352 or software-based emergency stop button 412 is pressed. For example, an alarm indication may be output to every network-connected screen in a red color or "alarm" text. Alarm indications may be logged in the event log. The alarm status may remain until reset. Only certain users may be permitted to reset the alarm status.

In addition to visual alarms output by the GUI, the system 200 may include pilot lights and lights stacks to indicate alarm conditions. For example, each of the flow centers 240 and each of the vacuum pumps 340 may include a pilot light or light stack. In the event of an alarm condition relating to one of the flow centers 240 or vacuum pumps 340, a visual alarm may be output by the pilot light or light stack associated with the flow center 240 or vacuum pump 340 experiencing the alarm condition.

In addition to visual alarms, an auditory alarm may also be output in response to an alarm condition. The operator interface terminals 270 may include a speaker to output the auditory alarms.

Process parameters may be transmitted to and from each of the network-connected hardware components of the system 200. Additionally, the system 200 may be configured to receive commands from authorized users via external systems (for example, via a web browser or remote desktop client). The system 200 may be configured to accept electrical signals as discrete commands from external systems. External systems may send electrical commands to initiate processes, reset alarms, and to activate alarms. The system 200 provides electrical signals as statuses as external systems. The system 200 may be configured to provide discrete process statuses.

Aspects of exemplary embodiments of the present invention overcome drawbacks of conventional systems by automatically adjusting the mass flow rates of each of the vacuum connections to the individual rates set by an operator. Additionally, aspects of exemplary embodiments of the present invention enable users to monitor and control aspects of the system via network-connected devices. Additionally, aspects of exemplary embodiments of the present invention enable a vacuum pump to be disconnected from power in response to a physical emergency button, a software-based emergency stop button available on network connected devices, and an automatic power disconnection in response to an abnormal mass flow reading that could potentially impact the vacuum pump.

The system 200 is also configured to automatically disconnect the power supplied to a vacuum pump 350 in response to a determination that any one of the vacuum connections 232 in flow communication with the vacuum pump 350 is experiencing an abnormally low mass flow rate (e.g., 0). Whereas conventional systems would shut down a vacuum pump only if all sample points were manually aborted, the system 200 provides additional protection against a vacuum pump 350 being damaged by an obstructed air sampling device 260 or vacuum connection 232.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, persons skilled in the art may affect such feature, structure, or characteristic in connection with other embodiments whether or not explicitly described.

Embodiments of the invention (particularly the controller(s) 210, the flow center(s) 240, the operator interface terminal(s) 270, the distributed PLC(s) 310, and the mass flow controller(s) 320, etc.) may be implemented in hardware, firmware, software, or any combination thereof, or may be implemented without automated computing equipment. Embodiments of the invention may also be implemented as instructions stored on a machine-readable medium, which may be read and executed by one or more processors or processing devices. A machine-readable medium may include any mechanism for storing or transmitting information in a form readable by a machine (e.g. a computing device). For example, a machine-readable medium or database (such as the database 290) may include read only memory (ROM); random access memory (RAM); hardware memory in PDAs, mobile telephones, and other portable devices; magnetic disk storage media; optical storage media; flash memory devices; electrical, optical, acoustical, or other forms of propagated signals (e.g. carrier waves, infrared signals, digital signals, analog signals, etc.), and others. Further, firmware, software, routines, instructions, may be described herein as performing certain actions. However, it should be appreciated that such descriptions are merely for convenience and that such actions in fact result from computing devices, processors, controllers or other devices executing the firmware, software, routines, instructions, etc.

It is appreciated that one advantage of the present invention includes simplifying the configuration of the air sampling devices and related components necessary for monitoring and controlling air sampling in a controlled environment by avoiding the need for certain components, such as conventional flow switches. The present invention also provides a high degree of flexibility to rearrange a display to show any number of individual parameters associated with air sampling and monitoring including, but not limited to, the location name, sample time, or duration of air quality tests.

These and other advantages of the present invention will be apparent to those skilled in the art from the foregoing specification. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

What is claimed is:

1. A system for sampling air at multiple locations in a controlled environment comprising:
 a plurality of air sampling devices, each configured to draw a volume of air from within a controlled environment;

a plurality of vacuum connections, each of the plurality of vacuum connections configured to receive the volume of air from one of the plurality of air sampling devices;

a vacuum pump, outside of the controlled environment, configured to draw each volume of air from each of the plurality of air sampling devices via the plurality of vacuum connections;

a plurality of flow sensors, each of the plurality of flow sensors configured to sense a mass flow rate of the volume of air received by one of the vacuum connections;

a graphical user interface that provides functionality for a user to specify one or more setpoints indicative of a desired mass flow rate at each of a plurality of the air sampling devices;

a plurality of flow control valves, each of the plurality of flow control valves configured to initiate an air sampling cycle at one of the air sampling devices and control the mass flow rate of the volume of air received by the corresponding vacuum connection in response to the desired mass flow rate specified by the user via the graphical user interface.

2. The system of claim 1, wherein the graphical user interface further provides functionality for the user to abort an air sampling cycle at the one or more of the air sampling devices.

3. The system of claim 1, wherein the graphical user interface provides the functionality to specify the one or more setpoints via the internet.

4. The system of claim 1, wherein the graphical user interface is provided by a server configured to authenticate the user and determine whether the user is permitted to issue commands.

5. The system of claim 1, further comprising:
a database that stores data indicative of the mass flow rates of the volumes of air received by the plurality of vacuum connections,
wherein the graphical user interface displays the data indicative of the mass flow rates.

6. The system of claim 1, wherein the system is configured to:
determine whether the mass flow rate of the volume of air received by one or more of the vacuum connections deviates from the desired flow rate beyond acceptable alarm limits; and
output an alarm to the user via the graphical user interface in response to a determination that the mass flow rate deviates from the desired flow rate beyond the acceptable alarm limit.

7. The system of claim 1, further comprising:
a plurality of actuators, each of the plurality of actuators configured to open and close one of the flow control valves;
a programmable logic controller (PLC) configured to:
receive the setpoints indicative of the desired mass flow rates at each of the one or more air sampling devices;
receive measured flow rates from the plurality of flow sensors indicative of the mass flow rates of each of the vacuum connections;
determine errors indicative of the differences between the measured flow rates and the setpoints;
output control signals to the plurality of actuators to reduce the differences between the measured flow rates and the setpoints.

8. The system of claim 7, wherein:
the plurality of air sampling devices comprises a first air sampling device and a second air sampling device;

the plurality of vacuum connections comprises a first vacuum connection configured to receive the volume of air from the first air sampling device and a second vacuum connection configured to receive the volume of air from the second air sampling device, the first and second vacuum connections in flow communication with the vacuum pump via a manifold;

the PLC is configured to reduce the difference between the measured flow rate of the volume of air received by the first vacuum connection and the setpoint indicative of the desired mass flow rate at the first air sampling device caused by a change in the volume of air through the second vacuum connection.

9. The system of claim 7, wherein the each of the flow control valves are configured to adjust such that a change in position of the flow control valve is:
proportional to the size of the difference between the set point and the measured flow rate of the vacuum connection corresponding to the respective flow control valve; or
proportional to a rate of change of the difference between the set point and the measured flow rate of the vacuum connection corresponding to the respective flow control valve.

10. The system of claim 1, wherein the system is configured to disconnect power to the vacuum pump in response to a determination that the mass flow rate of the volume of air received by one of the vacuum connections in flow communication to the vacuum pump is below a predetermined threshold.

11. A method for sampling air at multiple locations in a controlled environment, the method comprising:
drawing volumes of air, by a vacuum pump outside a controlled environment, from a plurality of air sampling devices within the controlled environment, via a plurality of vacuum connections;
receiving, by the plurality of vacuum connections, the volumes of air from each of the plurality of air sampling devices;
sensing, by a plurality of flow sensors, the mass flow rates of the volumes of air received by each of the vacuum connections;
providing a graphical user interface for display on a computing device;
receiving, from a user via the graphical user interface, one or more setpoints indicative of a desired mass flow rate at each of a plurality of the air sampling devices;
initiating an air sampling cycle at one of the air sampling devices; and
controlling, by one of a plurality of flow control valves, the mass flow rate of the volume of air received by the corresponding vacuum connection in response to the desired mass flow rate specified by the user via the graphical user interface.

12. The method of claim 11, further comprising:
receiving, from the user via the graphical user interface, an additional command to abort an air sampling cycle at the one or more of the air sampling devices; and
aborting an air sampling cycle in response to the command received from the user via the graphical user interface.

13. The method of claim 11, wherein the one or more setpoints are received via the internet.

14. The method of claim 11, further comprising:
authenticating the user; and
determining whether the user is permitted to issue commands.

15. The method of claim 11, further comprising:
storing data indicative of the mass flow rates of the volumes of air received by the plurality of vacuum connections,
displaying the data indicative of the mass flow rates via the graphical user interface.

16. The method of claim 11, wherein the system is configured to:
determining whether the mass flow rate of the volume of air received by one or more of the vacuum connections deviates from the desired flow rate beyond acceptable alarm limits; and
outputting an alarm to the user via the graphical user interface in response to a determination that the mass flow rate deviates from the desired flow rate beyond the acceptable alarm limit.

17. The method of claim 11, wherein controlling the mass flow rates comprises:
receiving, from a plurality of flow sensors, measured flow rates indicative of the mass flow rates of each of the vacuum connections;
determining errors indicative of the differences between the measured flow rates and the setpoints; and
outputting control signals to the plurality of flow control valves to reduce the differences between the measured flow rates and the setpoints.

18. The method of claim 17, wherein the difference between the setpoint indicative of the desired mass flow rate at a first air sampling device and the measured flow rate of the volume of air received by a first vacuum connection receiving the volume of air from the first air sampling device is caused by a change in the volume of air through a second vacuum connection that is in flow communication with the first vacuum connection via a manifold.

19. The method of claim 17, further comprising:
adjusting one or more of the flow control valves such that a change in position of the flow control valve is:
proportional to the size of the difference between the set point and the measured flow rate of the vacuum connection corresponding to the respective flow control valve; or
proportional to a rate of change of the difference between the set point and the measured flow rate of the vacuum connection corresponding to the respective flow control valve.

20. The method of claim 11, further comprising:
determining that the mass flow rate of the volume of air received by one of the vacuum connections in flow communication to the vacuum pump is below a predetermined threshold; and
disconnecting power to the vacuum pump in response to the determination that the mass flow rate of the volume of air received by one of the vacuum connections in flow communication to the vacuum pump is below the predetermined threshold.

* * * * *